US010950027B1

(12) United States Patent
Spear et al.

(10) Patent No.: US 10,950,027 B1
(45) Date of Patent: *Mar. 16, 2021

(54) PERIOPERATIVE MOBILE COMMUNICATION SYSTEM AND METHOD

(71) Applicant: TeleTracking Technologies, Inc., Pittsburgh, PA (US)

(72) Inventors: Steven Edward Spear, Lindstrom, MN (US); Michael James Weber, Woodbury, MN (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/856,798

(22) Filed: Apr. 23, 2020

Related U.S. Application Data

(63) Continuation of application No. 15/934,064, filed on Mar. 23, 2018, now Pat. No. 10,636,194, which is a continuation of application No. 14/694,607, filed on Apr. 23, 2015, now Pat. No. 9,928,636.

(60) Provisional application No. 61/983,859, filed on Apr. 24, 2014.

(51) Int. Cl.
| | |
|---|---|
| *G06T 13/80* | (2011.01) |
| *G06Q 10/06* | (2012.01) |
| *G06Q 50/22* | (2018.01) |

(52) U.S. Cl.
CPC ......... *G06T 13/80* (2013.01); *G06Q 10/0633* (2013.01); *G06Q 50/22* (2013.01)

(58) Field of Classification Search
None
See application file for complete search history.

(56) References Cited

U.S. PATENT DOCUMENTS

| | | | | |
|---|---|---|---|---|
| 9,053,222 | B2 * | 6/2015 | Lynn | G16H 50/20 |
| 9,211,096 | B2 * | 12/2015 | Tremper | A61B 5/02055 |
| 2007/0159487 | A1 * | 7/2007 | Felt | G06T 13/80 |
| | | | | 345/474 |
| 2009/0222746 | A1 * | 9/2009 | Chirica | G16H 10/40 |
| | | | | 715/762 |
| 2014/0129942 | A1 * | 5/2014 | Rathod | H04N 21/44222 |
| | | | | 715/720 |
| 2014/0164011 | A1 * | 6/2014 | Guelich | G16H 40/20 |
| | | | | 705/2 |

(Continued)

OTHER PUBLICATIONS

R. K. Lomotey and R. Deters, "Composition of the Electronic Health Record: Mobile Efficiency in mHealth," 2013 IEEE 6th International Conference on Service-Oriented Computing and Applications, Koloa, HI, 2013, pp. 146-153. (Year: 2013).*

(Continued)

*Primary Examiner* — James A Thompson
(74) *Attorney, Agent, or Firm* — Ference & Associates LLC

(57) ABSTRACT

An embodiment provides a mobile application that animates change information in a way that specifically indicates a change in workflow information for various users. This animation of change information permits users, which are often busy healthcare professionals, to be quickly apprised of relevant changes to workflow status. The mobile application also allows users to communicate change information, e.g., for updating the status of a workflow item, which may then be propagated throughout a network, including mobile devices.

20 Claims, 12 Drawing Sheets

(56) References Cited

U.S. PATENT DOCUMENTS

2014/0249855 A1* 9/2014 Moore ............... G16H 15/00
705/3
2015/0371176 A1* 12/2015 Barrett .......... G06Q 10/063114
705/2

OTHER PUBLICATIONS

J. Sutherland and W. van den Heuvel, "Towards an Intelligent Hospital Environment: Adaptive Workflow in the OR of the Future," Proceedings of the 39th Annual Hawaii International Conference on System Sciences (HICSS'06), Kauia, HI, USA, 2006, pp. 100b-100b. (Year: 2006).*

J. L. Sánchez-Cervantes, G. Alor-Hernández and U. Juárez-Martínez, "ITOHealth: A Multimodal Location-Based System for Discovering Medical Entities," 2010 IEEE Electronics, Robotics and Automotive Mechanics Conference, Morelos, 2010, pp. 237-242. (Year: 2010).*

L. Constantinescu, J. Kim and D. Feng, "SparkMed: A Framework for Dynamic Integration of Multimedia Medical Data Into Distributed m-Health Systems," in IEEE Transactions on Information Technology in Biomedicine, vol. 16, No. 1, pp. 40-52, Jan. 2012. (Year: 2012).*

* cited by examiner

US 10,950,027 B1

PERIOPERATIVE MOBILE COMMUNICATION SYSTEM AND METHOD

CROSS REFERENCE TO RELATED APPLICATIONS

This application is a continuation application of co-pending U.S. patent application Ser. No. 15/934,064, filed on Mar. 23, 2018, entitled "PERIOPERATIVE MOBILE COMMUNICATION SYSTEM AND METHOD", which itself is a continuation application of U.S. Pat. No. 9,928,636, filed on Apr. 23, 2015, entitled "PERIOPERATIVE MOBILE COMMUNICATION SYSTEM AND METHOD", which itself claims priority to U.S. Provisional Patent Application No. 61/983,859, filed on Apr. 24, 2014, the contents of which are incorporated by reference herein.

BACKGROUND

Health care staff members, e.g., perioperative staff members, need to be apprised of real-time status changes. In this regard, the Orchestrate™ client/server application has been implemented to assist staff in managing their workflows.

The Orchestrate™ application has two basic modules. A perioperative services module allows users to track the current day's patients through the three primary stages of surgical procedures: the preoperative, intraoperative, and postoperative stages. An ambulatory clinic module allows users to track the current day's patients during their time at a clinic. Clinics can provide various diagnostic or therapeutic services such as X-ray, computerized tomography (CT scan), magnetic resonance imaging (MRI), electrocardiogram (EKG), and endoscopy.

The Orchestrate™ application combines advanced visual controls, care alerts, operational alerts and business intelligence to form the central nervous software for perioperative areas. Using the application, the staff is provided with useful information in managing their workflows, e.g., room availability, status of room cleanup, amount of time a patient has been in a location, etc.

BRIEF SUMMARY

In summary, an embodiment provides a method of animating change information presented in a mobile healthcare application, comprising: issuing, from a mobile client device running the mobile healthcare application, a request for a mobile client device specific change set, wherein the mobile client device provides workflow status information and wherein the request for the mobile client device specific change set is communicated to a server storing change information for a plurality of mobile client devices, wherein the mobile client device specific change set comprises at least one change occurring since a time of the last request; said request including an indicator specific to the mobile client device issuing the request; receiving, at the mobile client device, a response from the server, wherein the response comprises the mobile client device specific change set; associating, using the mobile client specific change set, at least one change included in the mobile client device specific change set with at least one graphical element displayed by the mobile healthcare application; and automatically animating on a display screen of the mobile client device, responsive to the associating and without additional user input, the at least one graphical element associated with the at least one change since the time of the last request; wherein at least one patient panel is displayed in the mobile healthcare application and wherein the at least one graphical element corresponds to at least one sub-element displayed within the at least one patient panel.

Another embodiment provides a server that produces and transmits change information animated by a mobile healthcare application, comprising: a network communication element; a processor; a memory operatively coupled to the processor, the memory storing instructions executable by the processor to: receive, using the network communication element, a request from a mobile client device for a mobile client device specific change set, wherein the mobile client device provides workflow status information and wherein the mobile client device specific change set comprises at least one change occurring since a time of the last request; said request including an indicator specific to the mobile client device issuing the request; identify a response for the mobile client device, wherein the response comprises the mobile client device specific change set and includes at least one change in the mobile client device specific change set that correspondingly affects at least one graphical element associated with the at least one change; and provide the response to the mobile client device; wherein at least one patient panel is displayed in the mobile healthcare application and wherein the at least one graphical element corresponds to at least one sub-element displayed within the at least one patient panel.

A further embodiment provides a non-transitory program product having a mobile healthcare application, comprising: a storage device that including processor executable instructions stored therewith, the processor executable instructions comprising: instructions that issue, from a mobile client device running the mobile healthcare application, a request for a mobile client device specific change set, wherein the mobile client device provides workflow status information and wherein the request for the mobile client device specific change set is communicated to a server storing change information for a plurality of mobile client patient devices, wherein the mobile client device specific change set comprises at least one change occurring since a time of the last request; said request including an indicator specific to the mobile client device issuing the request; instructions that receive, at the mobile client device, a response from the server, wherein the response comprises the mobile client device specific change set; instructions that associate, using the mobile client specific change set, at least one change included in the mobile client device specific change set with at least one graphical element displayed by the mobile healthcare application; and instructions that automatically on a display screen of the mobile client device, responsive to the associating and without additional user input, the at least one graphical element associated with the at least one change since the time of the last request; wherein at least one patient panel is displayed in the mobile healthcare application and wherein the at least one graphical element corresponds to at least one sub-element displayed within the at least one patient panel.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in

DETAILED DESCRIPTION

Figure 1:
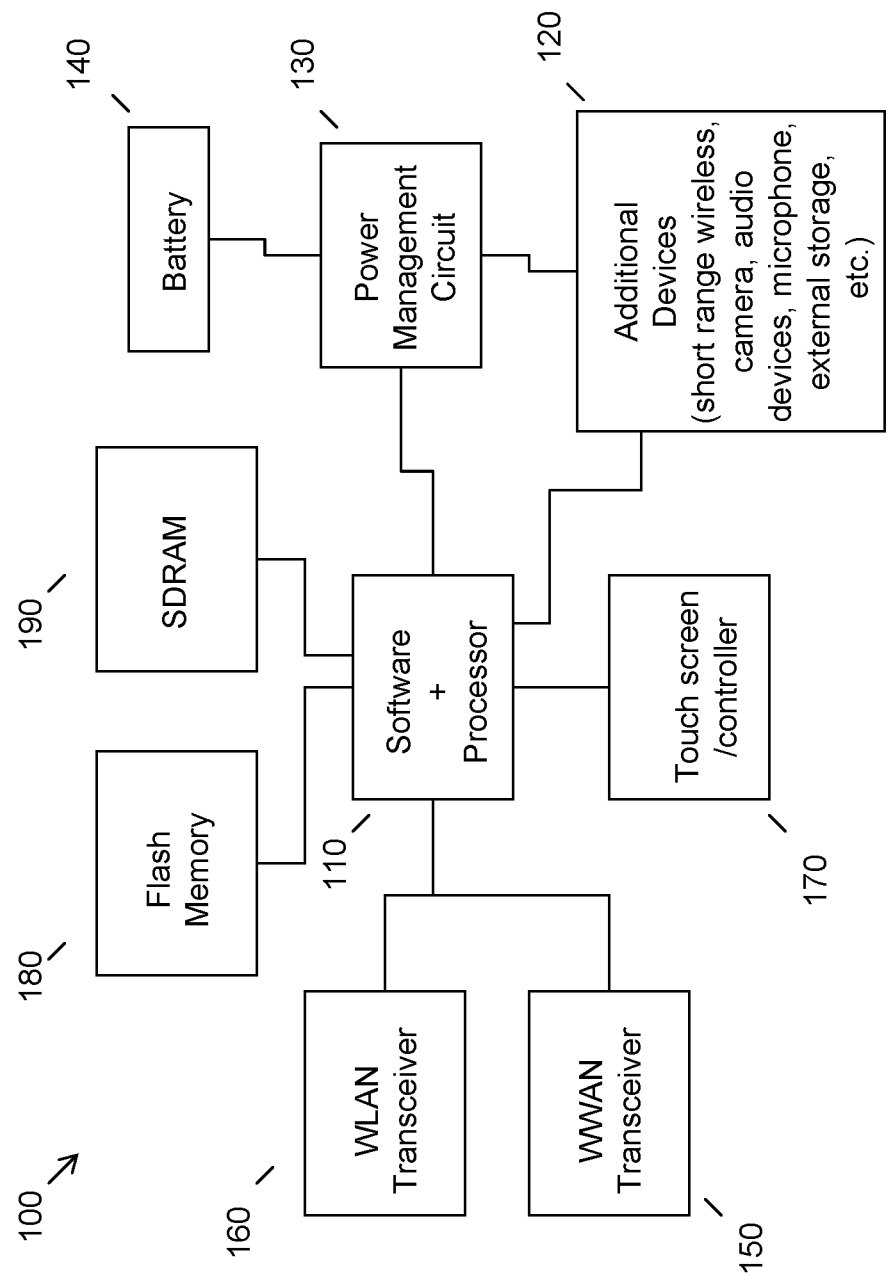
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well known structures, materials, or operations are not shown or described in detail to avoid obfuscation.

Staff may not always have access to a workstation or laptop. Status information needs to be configurable based on the unique needs of individual staff members. Staff members need to be made aware of any status changes that have occurred since they last viewed the information, e.g., at a stationary workstation or on his or her laptop. Staff also needs to be able to input status information, make additional requests (e.g., for staff or equipment) without having to access a workstation or laptop. Heretofore there has been no mobile application of this sort.

Accordingly, an embodiment provides a mobile application, e.g., for a smart phone, tablet, or hand held device, such that staff may be connected with workflow information services such as the Orchestrate™ application. In an embodiment, a central system (e.g., a server or collection of servers) generates view data for all possible configurations of the Orchestrate™ system and maintains the deltas or changes for all of those changes. A mobile client, e.g., a smart phone, may then receive the changes as needed, e.g., according to a policy, just-in-time to animate the status changes. For example, a mobile client may request change information from the server and/or have change information pushed thereto.

In this way, users are given a visual indication, e.g., using animation, to highlight just the changes from the last time the mobile application was opened or the screen was put to sleep. This may be particularly helpful to busy perioperative staff members that often have little time and much competition for their attention.

In an embodiment, the application for a mobile client is configurable, e.g., to accommodate particular users, particular user locations, particular protocols and procedures, accommodate particular security policies, etc. The views offered by the application on the mobile client may be filtered for specific users, e.g., based on roles, site locations, etc. For example, a specific view offered by the mobile application may be assigned to a logged in surgeon.

An embodiment provides a mobile application that animates change information in a way that specifically indicates a change in workflow information for various users. This animation of change information permits users, which are often busy healthcare professionals, to be quickly apprised of relevant changes to workflow status. The mobile application also allows users to communicate change information, e.g., for updating the status of a workflow item, which may then be propagated throughout a network, including mobile devices.

The illustrated example embodiments will be best understood by reference to the figures. The following description is intended only by way of example, and simply illustrates certain example embodiments.

While various other circuits, circuitry or components may be utilized in information handling devices, with regard to smart phone and/or tablet circuitry, an example illustrated in FIG. 1 includes a system 100 on a chip or circuit design found for example in tablets, smart phones or other mobile computing platforms. Software and processor(s) are combined in a single chip or circuit 110. Processors comprise internal arithmetic units, registers, cache memory, busses, I/O ports, etc., as is well known in the art. Internal busses and the like depend on different vendors, but essentially all the peripheral devices (120) may attach to a single chip or circuit 110. The circuitry 100 combines the processor, memory control, and I/O controller hub all into a single chip 110. Also, a system 100 of this type does not typically use SATA or PCI or LPC. Common interfaces, for example, include SDIO and I2C.

There are power management chip(s) or circuit(s) 130, e.g., a battery management unit, BMU, which manage power as supplied, for example, via a rechargeable battery 140, which may be recharged by a connection to a power source (not shown). In at least one design, a single chip or circuit, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additional devices 120 may be included, for example external storage. Commonly, system 100 will include a touch screen 170 for data input and display/rendering. System 100 also typically includes various memory devices, for example flash memory 180 and SDRAM 190.

Information handling device circuitry, as for example outlined in FIG. 1, may be used in mobile client devices such as a smart phone. By way of non-limiting example, FIG. 2-8 illustrate example screen shots of a mobile client application implemented on an IPAD® tablet. IPAD is a registered trademark of Apple, Inc. in the United States and other countries.

Figure 2:
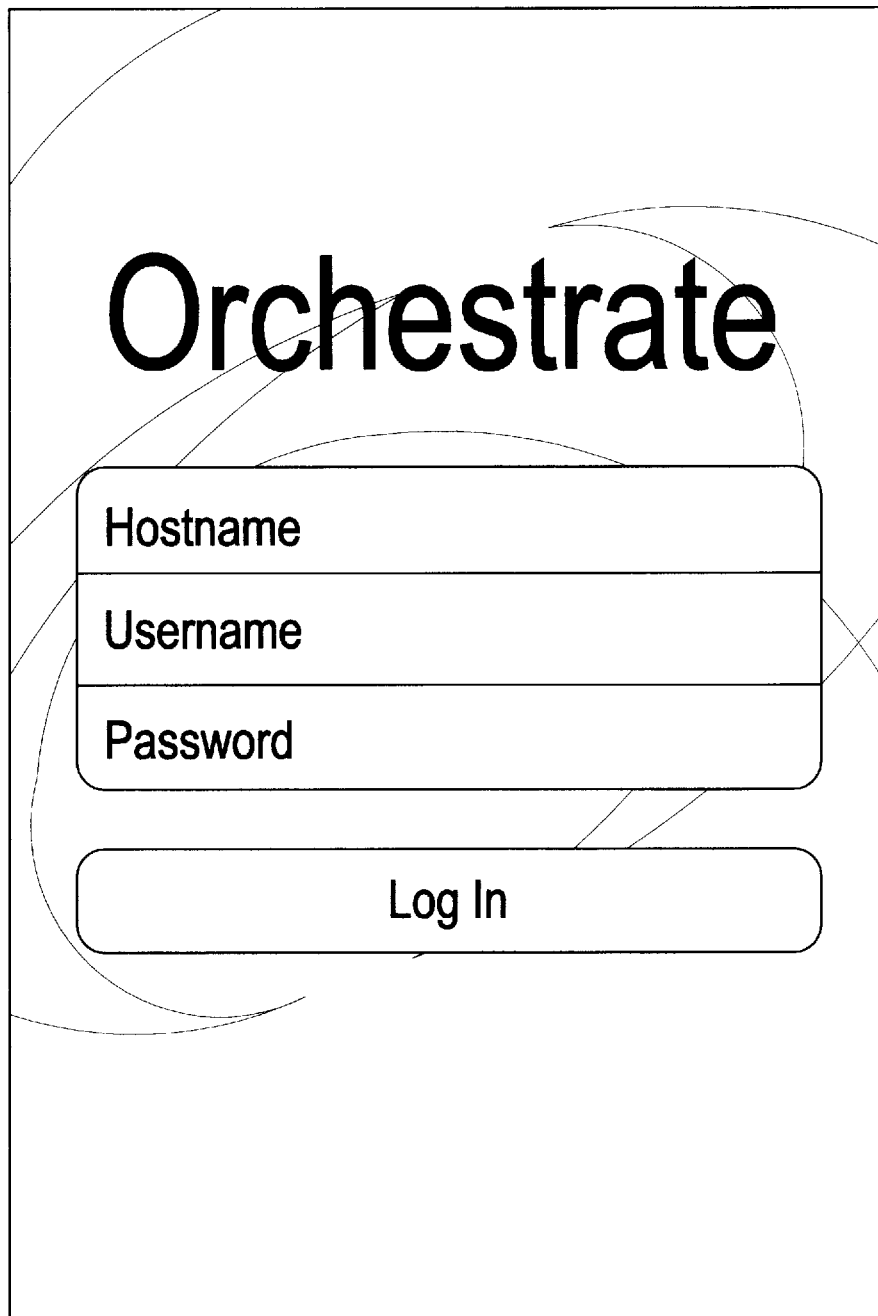
FIG. 2-FIG. 4 illustrate an example mobile application and information relating thereto.

Referring to FIG. 2, an example login screen is illustrated. The example login screen includes a hostname, e.g., location or unit such as a hospital group, a user name, e.g., of a particular staff member, and a password. As described herein, an embodiment may customize the mobile application or components thereof, e.g., the workflow items available in the mobile application, change information distributed to the mobile application, animation information used for animation, etc., based on the particular location or unit, the particular user, or other contextual information, e.g., location, time, substance of the information, etc.

Figure 3:
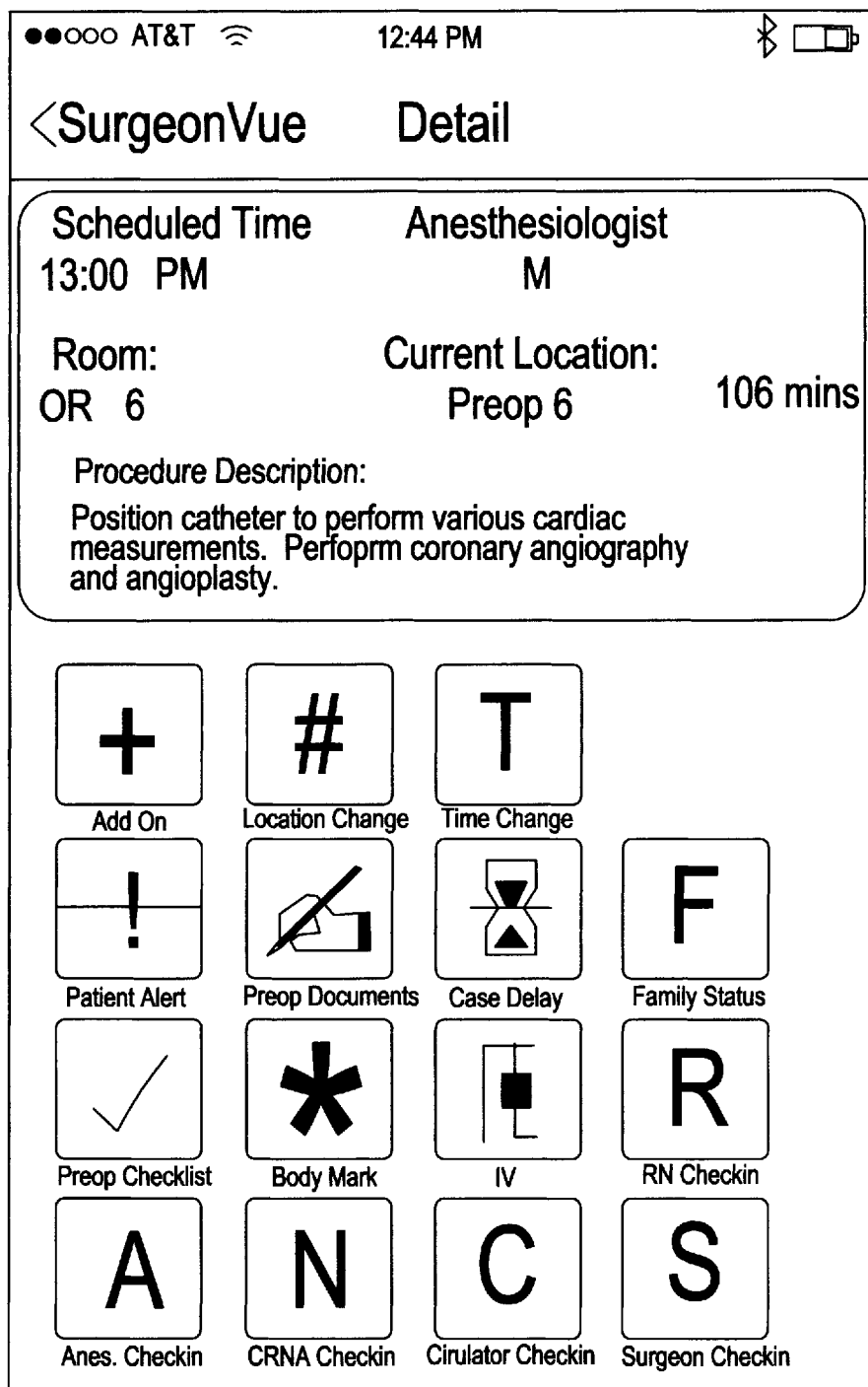

FIG. 3 shows an example of icons that may be used with the mobile application. In the example embodiment illustrated in FIG. 3, a surgeon view version of the mobile application may include but is not necessarily limited to the icons illustrated and the information corresponding thereto. For example, the mobile application includes icons in its interface that permit communication of patient alerts ("!"), preoperative document (status) information ("Preop Documents"), case delay information ("Case Delay"), family status information ("Family Status"), preoperative checklist information ("Preop Checklist"), body marking information ("Body Mark"), intravenous medication information (IV), nurse check in (status) information ("RN Checkin", "CRNA Checkin"), anesthesiologist check in (status) information ("Anes Checkin"), circulator status information ("Circulator Checkin"), and surgeon check in (status) information ("Surgeon Checkin"). The mobile application may also include icons such as add on, location change, and time change such that a user, e.g., a surgeon may view or make changes within the system depending on the workflow needs.

The mobile application illustrated in FIG. 3 shows that various workflow items, e.g., physician assigned, room, procedure description, etc., for a particular patient procedure or work item are provided in a convenient format.

Figure 4:
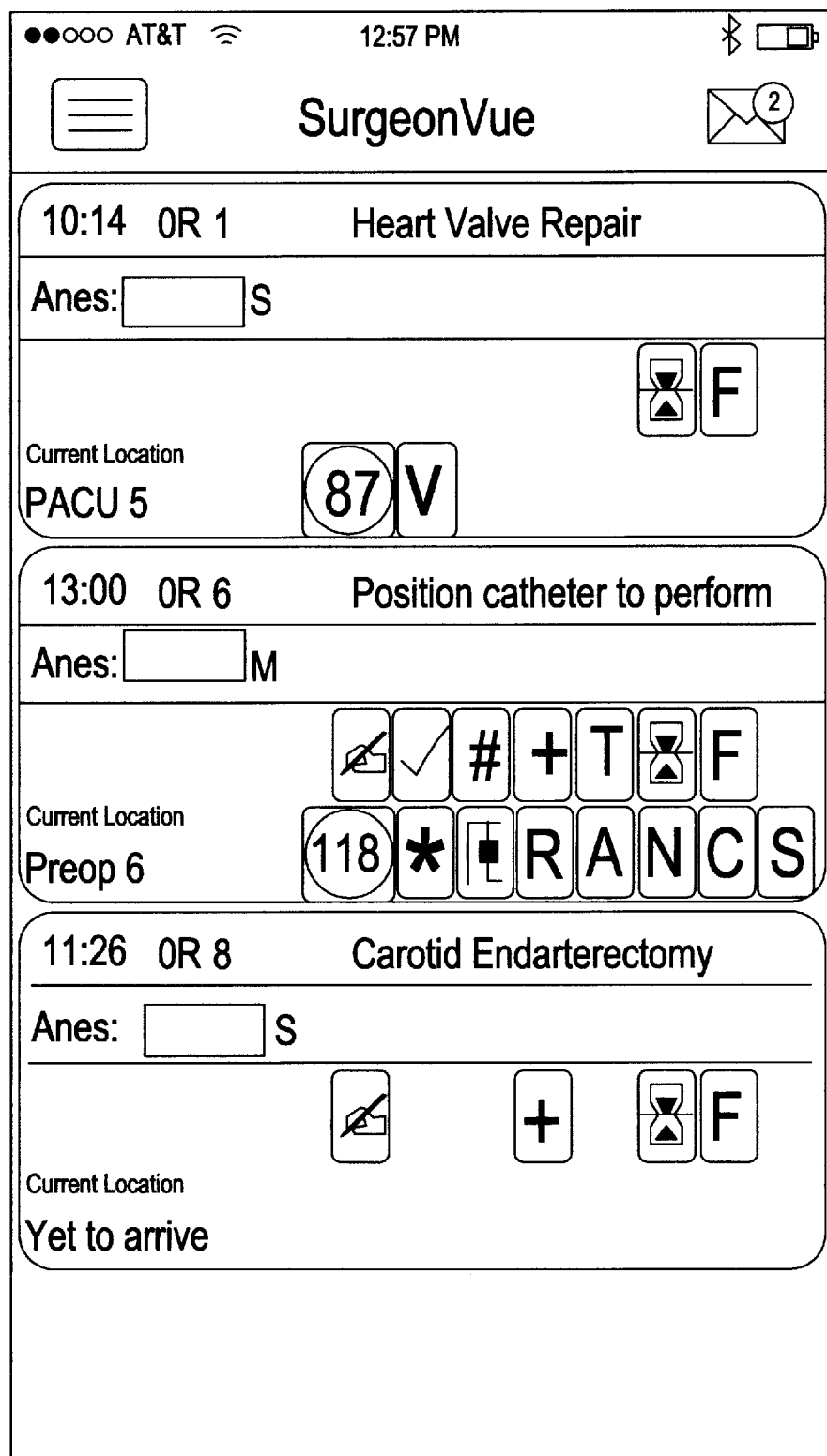

Illustrated in FIG. 4 is an example screen shot of a mobile application interface. As illustrated, panels of patient workflow information provide a time, topic or title, personal identifier (anesthesiologist assigned identifier in this example), location information, status information, as well as various icons (for example, those illustrated in FIG. 3) that provide quick access to various workflow information in a mobile environment.

Figure 5:
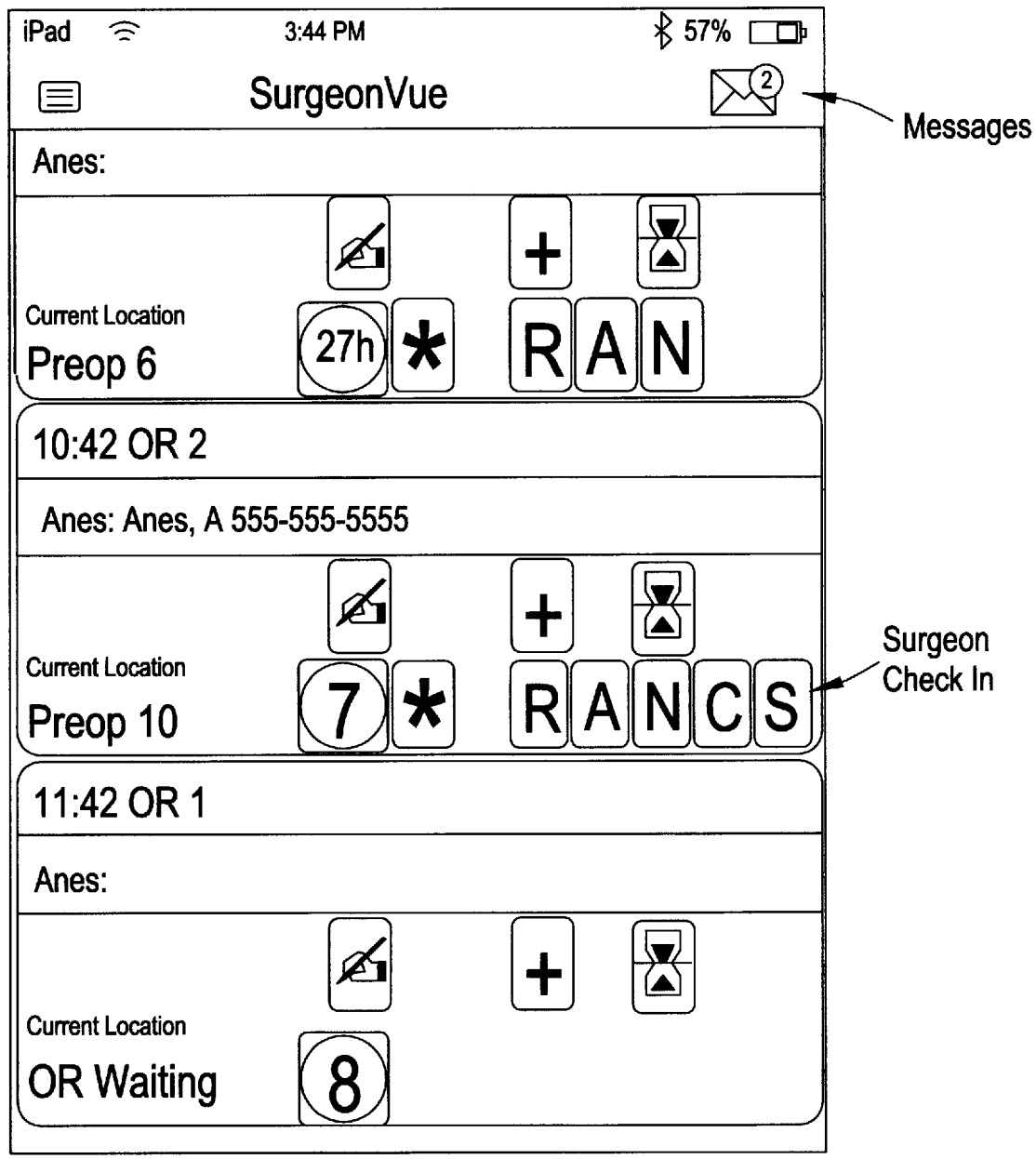
FIG. 5-FIG. 8 illustrate example screen shots for a mobile client application and animation of changes therein.

FIG. 5 illustrates another example screen shot in which a mobile application interface provides information regarding three workflow items, i.e., a patient in pre-op room 6, a patient in pre-op room 10, and a patient in the OR waiting room. This information is delivered (in whole or in part) for example by a server to a surgeon's smart phone or tablet running the application. Thus, the user (surgeon in this example) may be apprised of various patient statuses, patient locations or whether the patient is in-transit, and the staff member assigned to the respective locations and status information related to the staff member (e.g., check in status), as well as other pertinent information available from the central system, e.g., via click through (or otherwise interfacing with) the various icons located within the patient panels. In the example of FIG. 5 message and surgeon check in icons are specifically called out by way of example. Other pertinent information may include the actual location of staff assigned to a location. Location information and movements of patients and staff may be automatically updated in the central system and conveyed to the mobile application via integration of the server/client application with a real-time locating system (RTLS) utilizing RFID technology and tags or other RTLS technologies that are well known in the art.

Figure 6:
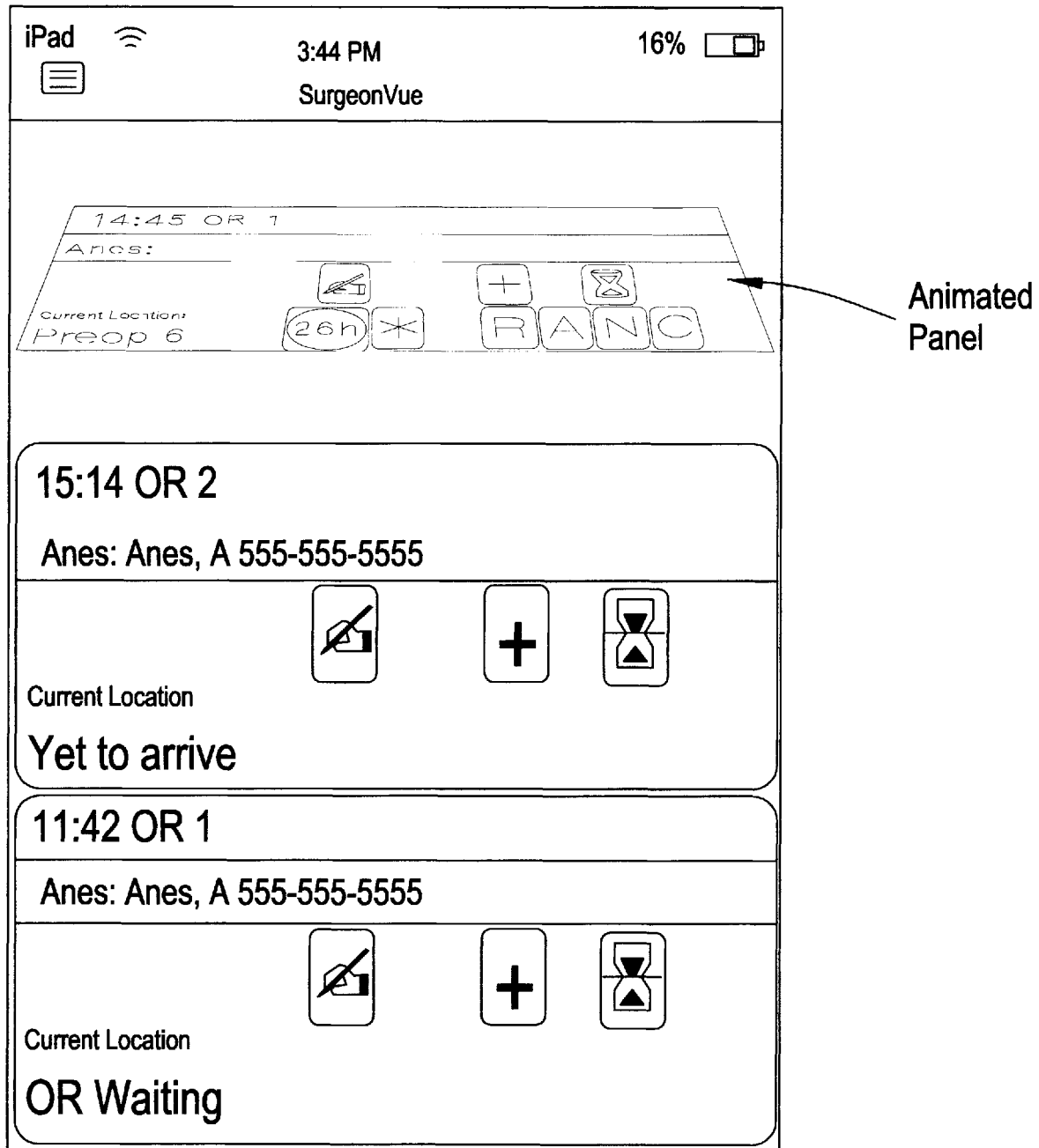

FIG. 6 illustrates how change information, including animation information, may affect the mobile application interface. In the example of FIG. 6 the appearance of the mobile interface is changed in such a way that the change is more easily noticeable to the user. For example, as shown in FIG. 6 the top panel is animated such that it moves back and away in a three-dimensional animation or key-stoning effect with respect to the bottom two panels. Here, for example, it is readily noticeable that the top panel has changed. This animated change may reflect an underlying change, e.g., in the status of the patient. For example, the patient that is the subject of the top panel may have been treated and moved on to a different area, thus warranting a change in the patient's status in the workflow. This information is communicated to a user's mobile device such that the mobile application interface may animate the change to quickly notify the user thereof. Therefore, the update in the mobile interface view reflects the change information communicated, e.g., from the server.

Figure 7:
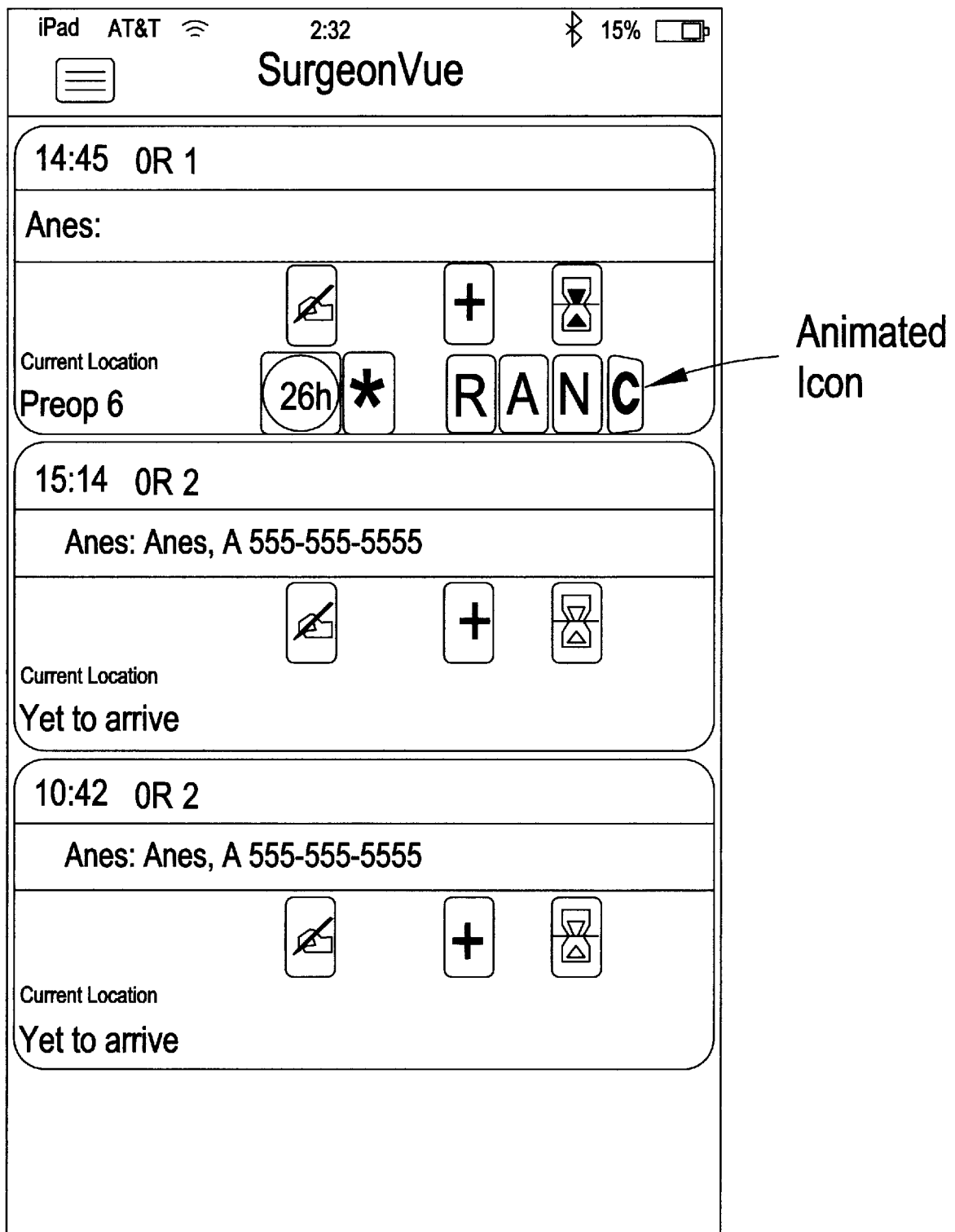

FIG. 7 illustrates that various sub-elements of a patient panel may be animated to distinguish changed information. In the example of FIG. 7, the "C" icon of the top panel has been animated such that it is rotated in a counterclockwise fashion with respect to the other icons of the panel, which remain in plan view. This may reflect a change in status of the workflow information associated with the particular icon, such as an indication that a Circulator has been requested or re-requested as in this example. Again the animation is used to visually distinguish the change information from the rest of the information that has not changed. More than one animation may be combined and the animations may be combined with other notifying information, e.g., haptic feedback, audible notifications, etc. In this embodiment for example, the animated "C" is animated such that it is rotated in a counterclockwise fashion but is also displayed with a colored background (shown in red in this example) to indicate that the Circulator has been re-requested.

Figure 8:
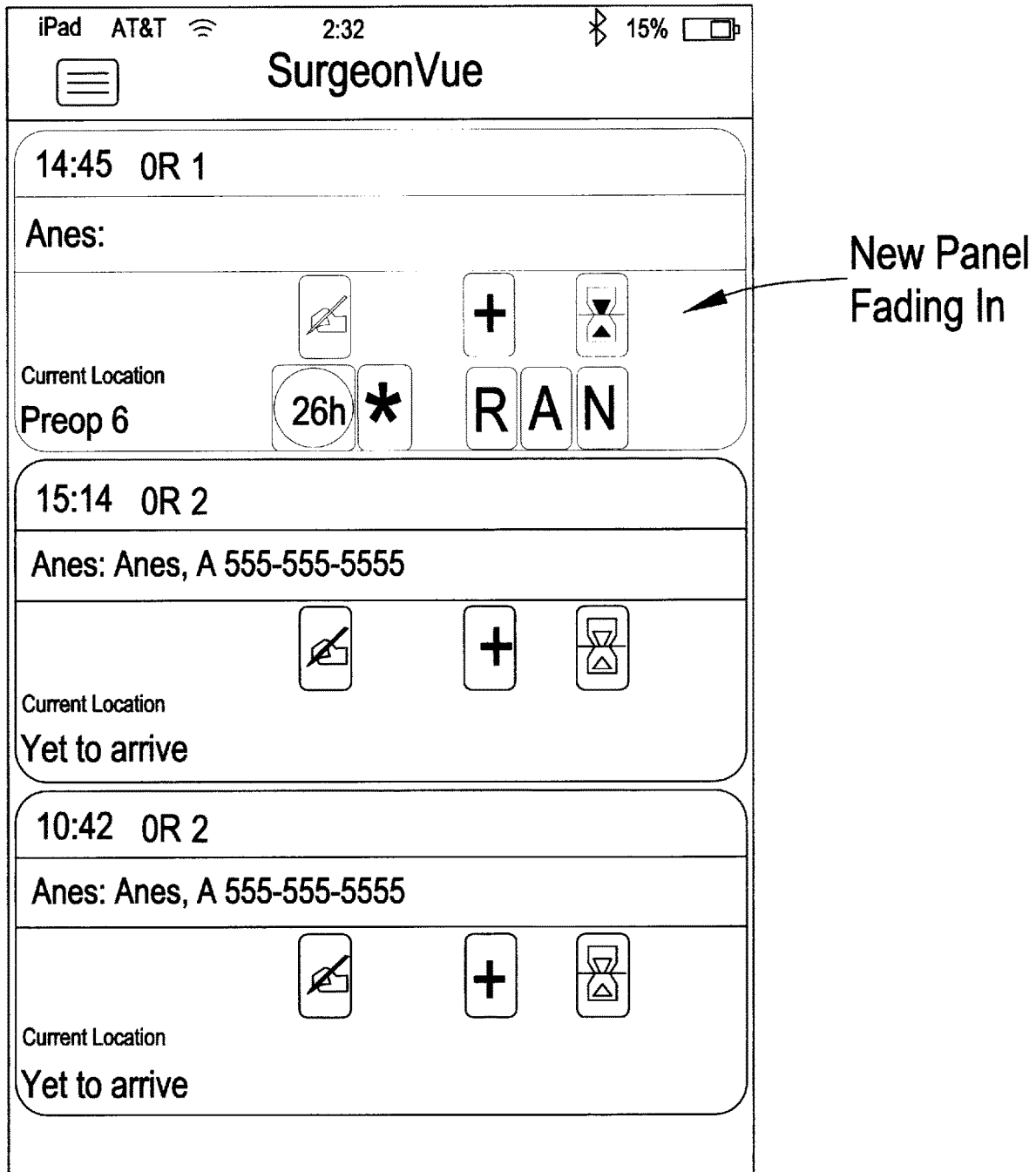

FIG. 8 illustrates an example of the mobile application interface where a new record is added. As illustrated, the new record is animated as fading into the top panel position of the mobile application interface. Here it may be appreciated that the new record quickly indicates by way of visual animation that the new patient record has arrived. This may facilitate the user noticing that a new record has populated the list, thus making it easier for the user to detect that the change has taken place with respect to the other information.

Figure 9:
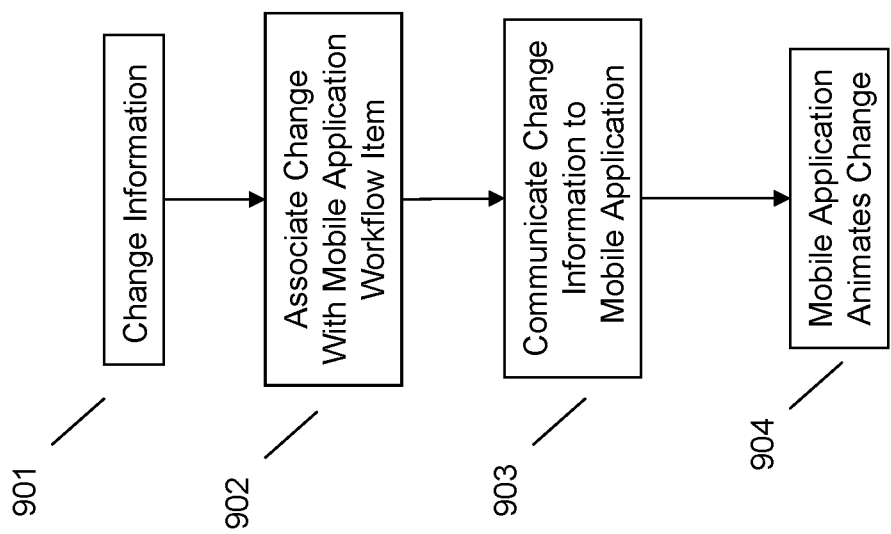
FIG. 9 illustrates an example method of animating change data for a mobile client application.

An example method of animating change data for a mobile client application is illustrated in FIG. 9. In the example of FIG. 9, change information is input to the central server at 901. This may correspond for example to a staff member updating information, e.g., at a workstation or via a mobile application such as described herein, e.g., a surgeon checking into a particular operating room.

At the central server, the change information is associated with appropriate mobile application workflow items at 902. For example, the surgeon check in information may be used to identify other users and elements, e.g., icons, panels, etc., such that these may be updated with the change information.

At 903, an embodiment communicates the change information to the mobile application(s). This communication may include animation information or may be a simple identifier of the element(s) to be changed, as well as addressing information for the destination(s), e.g., mobile device identifiers.

Having an indication of a change, at 904 the mobile application may animate the change using this indication. This may be implemented in a variety of ways. For example, the change information communicated from the server (either via a pushing or pulling mechanism) may include animation information. Alternatively or additionally, the local client application may have predetermined animation information that is triggered by the indication provided by the change information. For example, the predetermined animation may be included in a template that is populated with change information, with the animation being executed in a local client action. Thus, the mobile application may quickly apprise the user of the relevant change that has taken place, facilitating better management of the workflow items.

Figure 10:
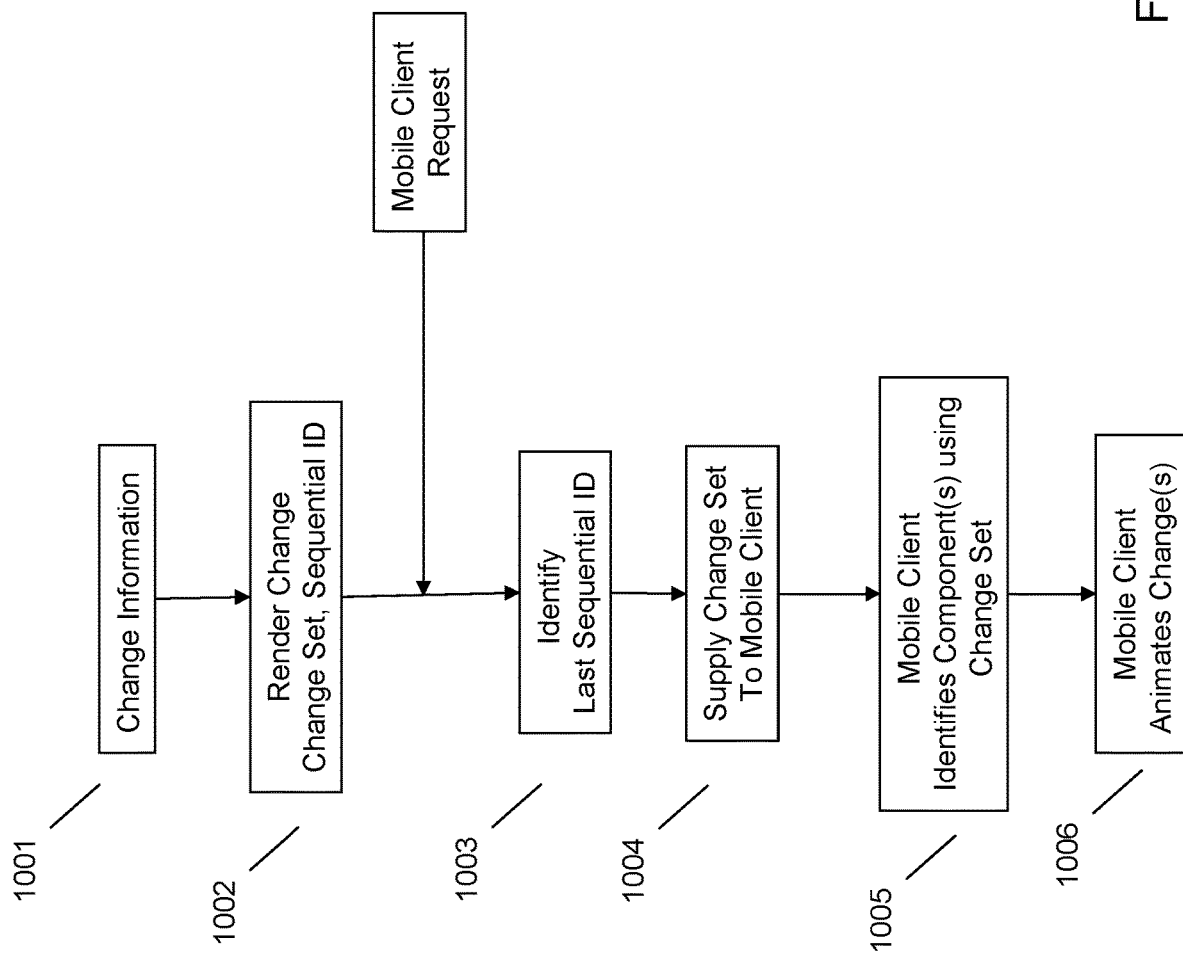
FIG. 10 illustrates an example method of preparing, communicating and implementing change animations for a mobile client.

By way of non-limiting example, and referring to FIG. 10, an underlying mobile client/server implementation, in terms of the change animations referred to herein, may be provided as follows. A universal interface virtual machine (UIVM) server (e.g., Orchestrate™ application server) receives information from the Orchestrate™ system, e.g., a workstation, a mobile client, etc., at 1001. This information may be used by a UIVM server at 1002 to render a change set and associate the change set with a sequential ID, which may be placed into a cache.

On an incoming request, e.g., as for example communicated by an Orchestrate™ application operating on a mobile client, the change set from UIVM server (e.g., via regular polling or when user opens application to see changes) may supply or identify the last sequence ID it received at 1003.

The UIVM server may then respond at 1004 with the change set required by the mobile client to make it consistent with the underlying UIVM data store. The Orchestrate™ mobile client may then use the change set at 1005 to identify the GUI component(s) that are to be changed, and thereafter animates the changes at 1006 (e.g. addition, deletion, or modification of GUI components).

Figure 11:
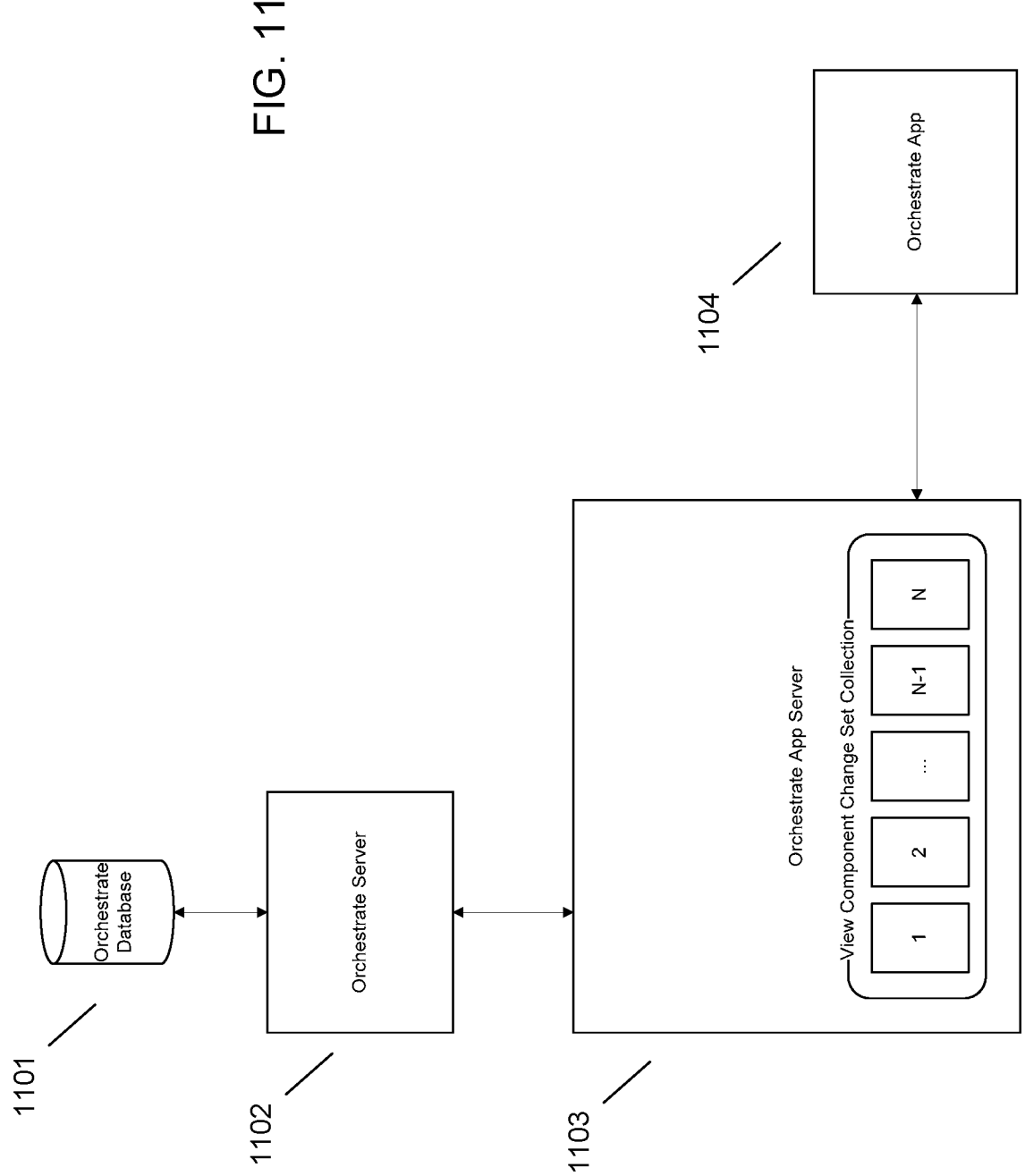
FIG. 11 and FIG. 12 illustrate an example relating to the information flow and operation of a system that communicates change information to mobile client(s).
Figure 12:
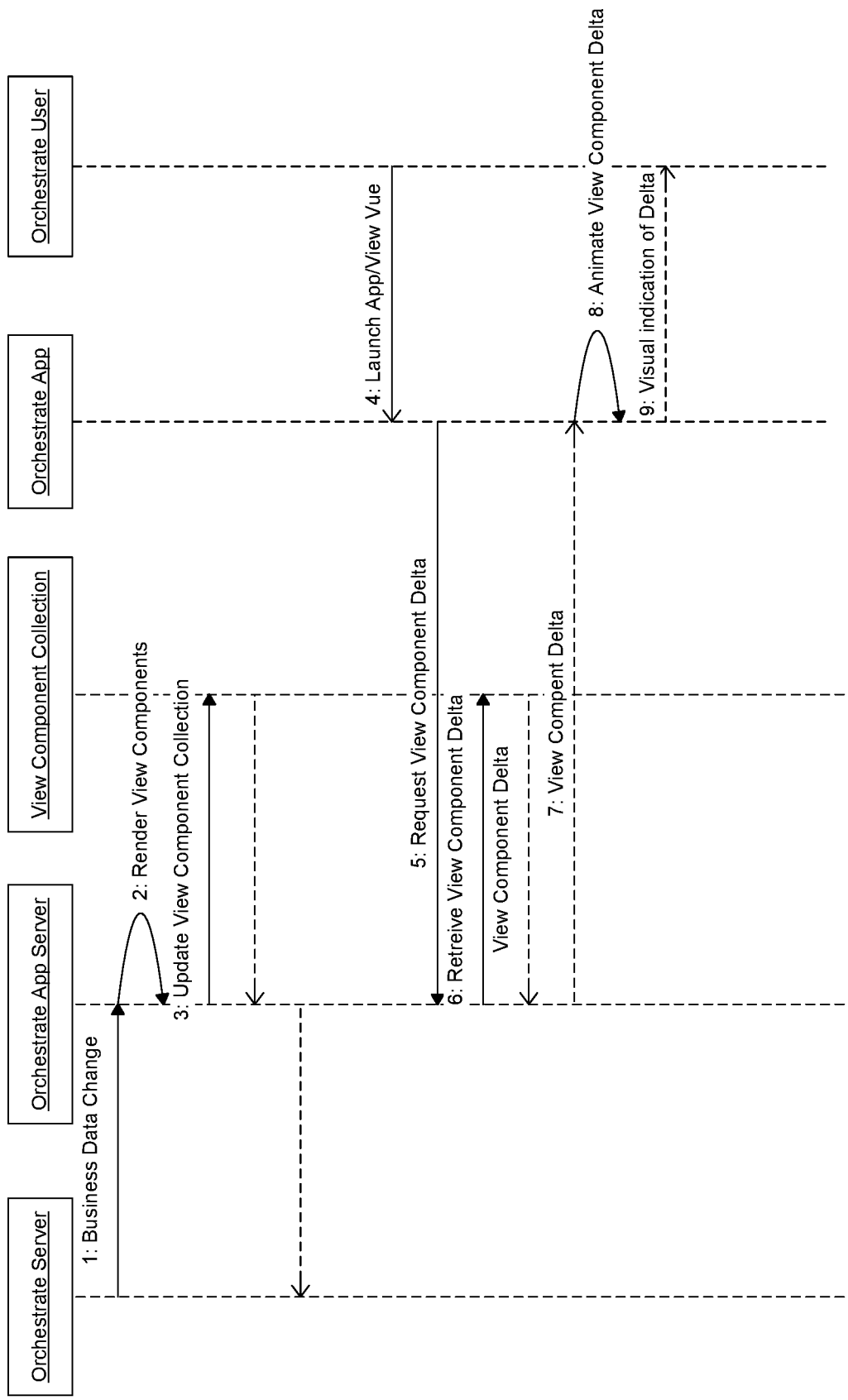

Referring collectively to FIG. 11 and FIG. 12, an example embodiment is illustrated relating to the information flow and operation of a system that communicates change information to mobile client(s), as described herein. As illustrated in this example, Orchestrate™ business data (change set) arrives at the Orchestrate™ App (application) Server (UIVM Server) 1103, e.g., from the Orchestrate™ server 1102. This data change set is the result of any action performed within the Orchestrate™ system. This data reflects the current state of the Orchestrate™ system. This data is essentially used to maintain a replicated data store of the underlying Orchestrate™ database 1101.

The Orchestrate™ App Server (UIVM Server) 1103 uses this information to generate the view component equivalent data consumed by the Orchestrate™ client 1104 (e.g., Orchestrate App of FIG. 11). This data is the presentation equivalent (e.g., rectangle position, color, pictures, strings, etc.) of the underlying Orchestrate™ data store 1101.

The Orchestrate™ App Server 1103 (UIVM Server) updates the current state of the view component collection. Additionally, it records this change set. At some time, the Orchestrate™ App 1104 user launches the Orchestrate™ App 1104 and/or selects to view the desired Orchestrate™ Vue (e.g., SurgeonVue™ illustrated in FIG. 4-FIG. 8). The Orchestrate™ App 1104 requests the view component change set from the Orchestrate™ App Server 1103 (UIVM Server) based on the view component change set sequence number it last received and processed.

Based on this sequence number, the Orchestrate™ App Server 1103 (UIVM Server) retrieves all of the view component change sets the Orchestrate™ App 1104 needs to reconcile its internal collection with the current state of the Orchestrate™ App Server's 1103 internal collection. The view component delta or change is returned to the Orchestrate App 1104. The Orchestrate App 1104 updates its internal state and calculates the appropriate animations to perform (e.g., cell add, update, delete, etc.). The visual animation draws attention to the Orchestrate App 1104 user to the changes made since the last time she viewed the data.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

Any combination of one or more non-signal device readable storage medium(s) may be utilized. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage medium is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a general purpose information handling device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method of animating change information presented in a mobile healthcare application, comprising:
   issuing, from a mobile client device running the mobile healthcare application, a request for a mobile client device specific change set, wherein the mobile client device provides workflow status information and wherein the request for the mobile client device specific change set is communicated to a server storing change information for a plurality of mobile client devices, wherein the mobile client device specific change set comprises at least one change occurring since a time of the last request;
   said request including an indicator specific to the mobile client device issuing the request;
   receiving, at the mobile client device, a response from the server, wherein the response comprises the mobile client device specific change set;
   associating, using the mobile client specific change set, at least one change included in the mobile client device specific change set with at least one graphical element displayed by the mobile healthcare application; and
   automatically animating on a display screen of the mobile client device, responsive to the associating and without additional user input, the at least one graphical element associated with the at least one change since the time of the last request;
   wherein at least one patient panel is displayed in the mobile healthcare application and wherein the at least one graphical element corresponds to at least one sub-element displayed within the at least one patient panel.

2. The method of claim 1, wherein the animating the at least one sub-element is reflective of a change in the workflow status information associated with the at least one sub-element.

3. The method of claim 1, wherein the animating comprises visually distinguishing the at least one sub-element from other sub-elements displayed in the at least one patient panel.

4. The method of claim 1, further comprising combining the animation of the at least one sub-element with other notifying information.

5. The method of claim 1, wherein the animating comprises key-stoning the at least one graphical element.

6. The method of claim 1, wherein the at least one graphical element is one of a plurality of graphical elements currently displayed.

7. The method of claim 1, wherein said issuing occurs according to a policy.

8. The method of claim 7, wherein the policy is time-based.

9. The method of claim 1, wherein the mobile healthcare application comprises a role-based view.

10. The method of claim 1, wherein each of the plurality of patient panels is associated with an individual healthcare worker.

11. A server that produces and transmits change information animated by a mobile healthcare application, comprising:
    a network communication element;
    a processor;
    a memory operatively coupled to the processor, the memory storing instructions executable by the processor to:
    receive, using the network communication element, a request from a mobile client device for a mobile client device specific change set, wherein the mobile client device provides workflow status information and wherein the mobile client device specific change set comprises at least one change occurring since a time of the last request;
    said request including an indicator specific to the mobile client device issuing the request;
    identify a response for the mobile client device, wherein the response comprises the mobile client device specific change set and includes at least one change in the mobile client device specific change set that correspondingly affects at least one graphical element associated with the at least one change; and
    provide the response to the mobile client device;
    wherein at least one patient panel is displayed in the mobile healthcare application and wherein the at least one graphical element corresponds to at least one sub-element displayed within the at least one patient panel.

12. A non-transitory program product having a mobile healthcare application, comprising:
    a storage device that including processor executable instructions stored therewith, the processor executable instructions comprising:
    instructions that issue, from a mobile client device running the mobile healthcare application, a request for a mobile client device specific change set, wherein the mobile client device provides workflow status information and wherein the request for the mobile client device specific change set is communicated to a server storing change information for a plurality of mobile client patient devices, wherein the mobile client device specific change set comprises at least one change occurring since a time of the last request;
    said request including an indicator specific to the mobile client device issuing the request;
    instructions that receive, at the mobile client device, a response from the server, wherein the response comprises the mobile client device specific change set;

instructions that associate, using the mobile client specific change set, at least one change included in the mobile client device specific change set with at least one graphical element displayed by the mobile healthcare application; and instructions that automatically on a display screen of the mobile client device, responsive to the associating and without additional user input, the at least one graphical element associated with the at least one change since the time of the last request;

wherein at least one patient panel is displayed in the mobile healthcare application and wherein the at least one graphical element corresponds to at least one sub-element displayed within the at least one patient panel.

13. The program product of claim 12, wherein the animating the at least one sub-element is reflective of a change in the workflow status information associated with the at least one sub-element.

14. The program product of claim 12, wherein the animating comprises visually distinguishing the at least one sub-element from other sub-elements displayed in the at least one patient panel.

15. The program product of claim 12, further comprising combining the animation of the at least one sub-element with other notifying information.

16. The program product of claim 12, wherein the animating comprises key-stoning the at least one graphical element.

17. The program product of claim 12, wherein the at least one graphical element is one of a plurality of graphical elements currently displayed.

18. The program product of claim 12, wherein said issuing occurs according to a policy.

19. The program product of claim 12, wherein the mobile healthcare application comprises a role-based view.

20. The program product of claim 12, wherein the mobile client device specific change set is user specific.

* * * * *